United States Patent [19]
Miller et al.

[11] 3,981,820
[45] Sept. 21, 1976

[54] ANTISKID COATING

[75] Inventors: Richard C. Miller; Charles C. Payne, both of Chicago, Ill.

[73] Assignee: Nalco Chemical Company, Oak Brook, Ill.

[22] Filed: June 16, 1975

[21] Appl. No.: 587,320

Related U.S. Application Data

[62] Division of Ser. No. 390,897, Aug. 23, 1973, Pat. No. 3,930,063.

[52] U.S. Cl. .......................... 252/301.16; 73/150 R; 106/36; 106/287 S; 427/157; 427/158
[51] Int. Cl.$^2$ ..................... C09K 11/00; C09K 3/14
[58] Field of Search ............ 252/301.2 R, 301.2 W, 252/301.3 R, 301.3 W, 301.4 R, 301.16; 427/157, 158; 106/36, 287 S; 73/150 R

[56] References Cited

UNITED STATES PATENTS

| | | | |
|---|---|---|---|
| 3,421,908 | 1/1969 | Rusher | 106/287 S X |
| 3,421,909 | 1/1969 | Rusher | 106/287 S X |

*Primary Examiner*—John H. Mack
*Assistant Examiner*—Aaron Weisstuch
*Attorney, Agent, or Firm*—Kinzer, Plyer, Dorn & McEachran

[57] ABSTRACT

A large particle sized silica sol and a fluorescent dye are mixed together and applied as a coating to a substrate with the application monitored during coating by a light which renders the fluorescent dye visible; if the coating is blotched or uneven, corrections can be made during the run to provide a uniform coating.

4 Claims, No Drawings

ANTISKID COATING

This is a division of application Ser. No. 390,897, filed Aug. 23, 1973, now U.S. Pat. No. 3,930,063.

BACKGROUND OF THE INVENTION

This invention relates generally to coating of substrates with an antiskid material and more particularly concerns the coating of substrates with an antiskid material in the form of a silica aquasol, provision being made for observing the uniformity of the coating applied to the substrate.

It is quite common in coating applications to coat a substrate several times, often with a coating which is hard to see with human eye. While this is a common problem with a clear coating, it is also a problem when coatings of similar color to the substrate are made. Often in these coating operations the applicator becomes blocked causing a non-uniform coating to be applied and it is necessary to quickly discover that the application is not uniform so as to correct the applicator.

Some attempts to discover this have used an indicator spray which is sprayed on the coating and gives a characteristic color if the silica is present. However, these indicators have been confined to use on special test panels of the coated substrate which are run infrequently, usually at the start up of the coating application and at spaced intervals to recheck. These indicator sprays cannot be applied to a wet coating due to the solvent incompatability, so the coated substrate must be at least partially dried before the indicator spray is usable. These indicator sprays also form a permanent color change which renders any sprayed coated substrate unusable, so the test panels are usually discarded.

Accordingly it is an object of this invention to provide a composition and method for easily observing the uniformity of application of a silica sol coating. Another object is to provide a means for observing the uniformity of an aqueous silica sol coating application while the coating is still wet. An allied object is to provide a composition and method for observing the uniformity of a silica coating on a substrate without rendering the substrate unusable. A related object is to develop a composition which meets the above objects and one which does not have any adverse effects on the antiskid coating.

SUMMARY OF THE INVENTION

In accordance with the invention, a method for determining the uniformity of application of a silica aquasol coating on a substrate has been found which includes, preparing a liquid coating for application to the substrate and incorporating an indicator which becomes visible when irradiated with radiant energy of a predetermined wave length in the liquid coating. The coating and the indicator are then applied to the substrate and the applied coating is irradiated with the radiant energy of the predetermined wave length to render the indicator visible whereby any blotching or imperfections in application are readily apparent to a worker at an observation station. The applicator can be easily adjusted since the worker knows exactly where the problem occurs, and the imperfect coating on the substrate may be corrected by secondary applicators down the line from the observation station.

Other objects and advantages of the invention will become apparent upon reading and following detailed description. While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

DETAILED DESCRIPTION OF THE INVENTION

The preferred form of antiskid agent is that of an aqueous silica sol. Aqueous silica sols with particle diameters from 4 to 150 mu can be used; however, large particle size sols are preferred due to their excellent antiskid performance. The preferred range of particle diameters is from 50 to 150 mu. Of course, other antiskid compositions such as those based on aluminum oxide, other metal oxides or coated silica sols can also be used.

A preferred fluorescent dye is that of Calcofluor White ST, manufactured by American Cyanamid, but other fluorescent dyes can be used. The amount of dye added to the product should be low enough that the properties of the product and of the substrate are not adversely affected but large enough that the dye can be seen on a substrate with the irridiating radiation. This level depends upon the particular dye chosen, the amount of dilution of the antiskid product and the long term stability of the product.

An ultraviolet light is a convenient source of irradiation.

The fluorescent dye is usually applied as a solution rather than a dry powder. It was found that very low fluorescence was observable on the substrate at equivalent levels of fluorescent dye in the powder form being added to the antiskid mixture. A fluorescent brightener is optionally added to the fluorescent dye solution. A preferred mixture is a fluorescent dye dissolved in water containing small amounts of cellosolve and triethanolamine and a fluorescent brightener to give a solution which contains approximately 30% by weight fluorescent material. The cellosolve and triethanolamine are present to facilitate the initial dissolution of the fluorescent dye in water. A preferred brightener is a sulfonated triazinylstilbene known as fluorescent brightener 28, Color Index No. 40622. Some of these brighteners are available from E. I. Dupont and are known as Paper White BN, Paper White BP, Pontamine White BT and Pontamine White BTS.

A preferred antiskid and fluorescent dye coating was prepared consisting of approximately 40% silica concentration and a fluorescent dye concentration of 0.7%.

EXAMPLE 1

A silica sol solution containing 50% $SiO_2$ having a pH of 8.5, a viscosity of 10 cps and an average particle size of 70 to 120 mu was diluted with water to a 42% silica level, and a dye solution containing 30% Calcofluor White ST dissolved in water containing small amounts of cellosolve and triethanolamine was added with an appropriate amount of water to give a final 40% silica level to the application mixture, and mixed. The final concentration of Calcofluor White ST was 0.7% with approximately 0.2% by weight active fluorescent material. It is usually necessary to mix the fluorescent dye with the water prior to addition to the silica sol in order to prevent formation of gel particles, but accelerated aging tests showed a stability of the mixture of greater than one year.

The mixture of Example 1 was applied to a cellulosic substrate by application means such as a sponge, felt, roller, knife edge or sprayer. An operator can irradiate the coated substrate with ultraviolet light to determine if the applicator is working properly and applying a uniform coating to the entire substrate. Adjustments can be made on the applicator while the machine is running in order to correct any non-uniformity of application.

Antiskid tests were carried out on kraft wrapping paper coated with the above mixture containing a fluorescent dye and also the above mixture without a fluorescent dye. The slide angle was not adversely affected by the dye. Not only were completely uncoated areas easily observable, but also differences in thickness of the application were apparent from the intensity of the fluorescence.

When the prior art indicator sprays were used to check the coating levels, no difference was observed in the color and intensity of the separate indicator whether or not the coating contained a fluorescent dye. However, ultraviolet illumination of the substrate was capable of detecting the coating of antiskid agent at higher dilutions where the reaction of the indicator spray failed but the fluorescence was still present.

Thus, it is apparent that there has been provided, in accordance with the invention, a coating that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

We claim:

1. A liquid coating composition for application to substrates to impart antiskid properties thereto, comprising: an aqueous silica sol containing a fluorescent dye.

2. A composition as in claim 1 which additionally includes a fluorescent brightener.

3. A composition as in claim 1 wherein silica from said silica sol is about 40% by weight of the total composition and said fluorescent dye is about 0.2% by weight of the total composition.

4. A composition as in claim 1 wherein said silica is in the form of particles with diameters from 4 to 150 mu.

* * * * *